United States Patent [19]

Kolesar, Jr.

[11] Patent Number: 4,871,427
[45] Date of Patent: Oct. 3, 1989

[54] ION DETECTION USING A DIFFERENTIAL RESISTANCE MEASUREMENT OF AN ION EXCHANGE MEMBRANE

[75] Inventor: Edward S. Kolesar, Jr., Beavercreek, Ohio

[73] Assignee: United States of America as represented by the Secretary of the Air Force, Washington, D.C.

[21] Appl. No.: 211,512

[22] Filed: Jun. 24, 1988

[51] Int. Cl.$^4$ .............................................. G01N 27/04
[52] U.S. Cl. .................... 204/1 T; 204/225; 204/406; 204/409; 204/411; 204/412; 324/71.1; 324/439; 324/443
[58] Field of Search ............... 204/406, 409, 411, 412, 204/1 F, 1 B, 1 K, 225, 1 T, ; 324/439, 443, 71.1

[56] References Cited

U.S. PATENT DOCUMENTS

| | | | |
|---|---|---|---|
| 3,558,279 | 1/1971 | McRae et al. | 324/443 X |
| 3,992,662 | 11/1976 | Koepnick et al. | 324/30 R |
| 4,057,481 | 11/1977 | Lee et al. | 204/296 |
| 4,102,771 | 7/1978 | Honig | 204/299 EC |
| 4,149,950 | 4/1979 | Potts | 204/195 G |
| 4,160,205 | 7/1979 | Hobbs et al. | 324/65 R |
| 4,220,916 | 9/1980 | Zimmermann et al. | 324/71 R |
| 4,401,548 | 8/1983 | Brezinski | 204/435 |
| 4,404,065 | 9/1983 | Matson | 204/1 T |
| 4,433,299 | 2/1984 | Kawai et al. | 324/464 |
| 4,441,507 | 4/1984 | Steffin | 128/734 |
| 4,472,356 | 9/1984 | Kolesar, Jr. | 422/88 |
| 4,488,556 | 12/1984 | Ho | 128/635 |
| 4,549,427 | 10/1985 | Kolesar, Jr. | 73/23 |

FOREIGN PATENT DOCUMENTS 2753842 11/1977 Fed. Rep. of Germany .
155846 12/1981 Japan .

OTHER PUBLICATIONS

"Conductance and Water Transfer in a Leached Cation-Exchange Membrane", by J. H. B. George and R. A. Courant, The Journal of Physical Chemistry, Jan. 67, pp. 246-249.
"Electrostatic Phenomena in Ion Exchange Membranes", by S. D'Alessandro and A. Tantillo, Elseveir Publishing Co, Amsterdam, Oct. 1969.
"Permeation Through a Membrane with Mixed Boundary Conditions:", by R. M. Barrer, Barrie and M. G. Rogers, Faraday Society, British, vol. 58, No. 480, part 12, Dec. 1962, pp. 2473-2483.
Von G. Manecke et al., Z. Electrochem., vol. 55, No. 6, p. 475, (Aug. 1951).

Primary Examiner—John F. Niebling
Assistant Examiner—David G. Ryser
Attorney, Agent, or Firm—G. B. Hollins; Donald J. Singer

[57] ABSTRACT

An electrochemical differential resistance measurement arrangement usable for detecting low concentration ionic impurities such as chemical warfare agents in liquids such as water. The disclosure includes details of electrochemical cells used in the liquid resistance measurement arrangement including one cell with fixed electrode positions and a selective ion transmitting membrane one cell with adjustable electrode position, and a combination cell. A differential bridge electrical circuit, together with a preferred form of alternating current energization therefor, an effluent circuit therefor and a balancing method sequence of steps for the bridge, are also included.

24 Claims, 3 Drawing Sheets

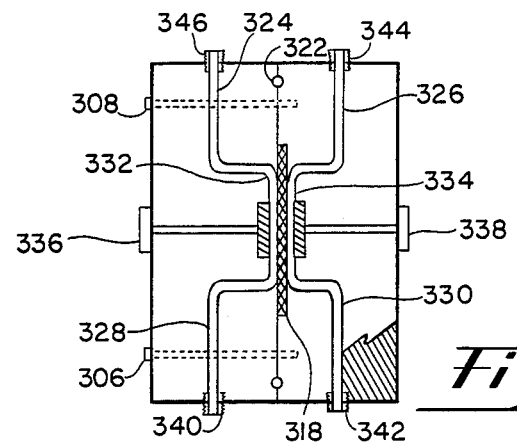
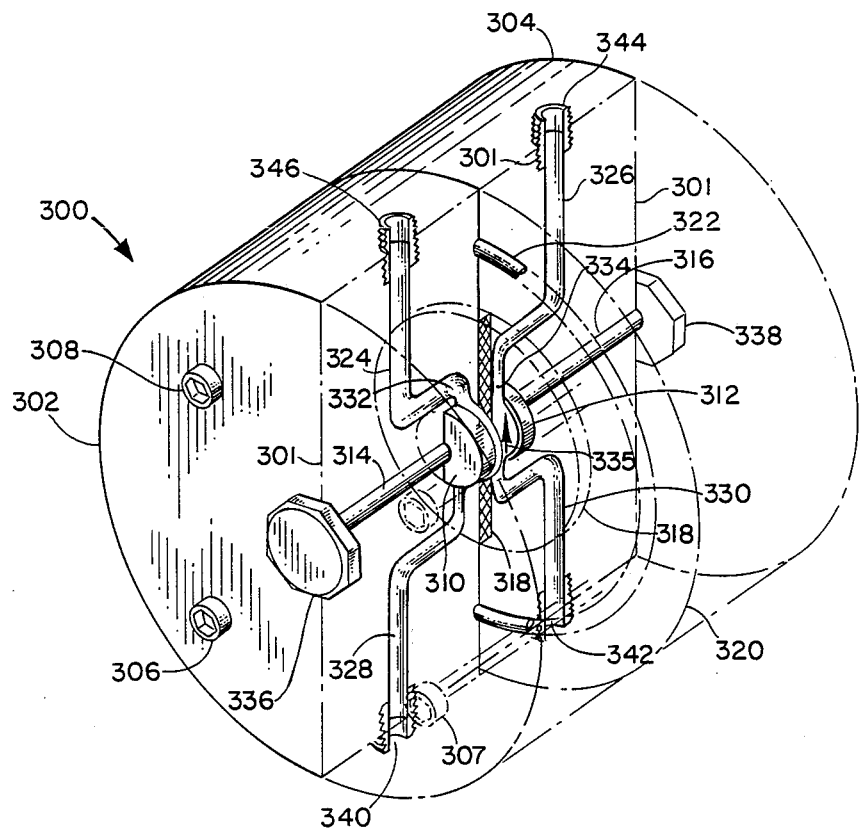

ION DETECTION USING A DIFFERENTIAL RESISTANCE MEASUREMENT OF AN ION EXCHANGE MEMBRANE

RIGHTS OF THE GOVERNMENT

The invention described herein may be manufactured and used by or for the Government of the United States for all governmental purposes without the payment of any royalty.

BACKGROUND OF THE INVENTION

This invention relates to the detection of small ionic concentrations of impurities in electrolytic fluids using electrical resistance measurement of electrolytic membranes, and additionally, to the application of such detection to the field of chemical warfare agent presence sensing.

The present day living and working environment exposes humans to a variety of gaseous vapor and liquids, some of which are of known toxicity or pose other health consequences and, are therefore, of intense concern regarding exposure dosage level and environmental presence. The organophosphorous pesticides and the structurally related chemical warfare agents are a particularly important group of potential environmental contaminates. The organophosphorous compounds and similar compounds involving the elements, chlorine, sulfur and flourine, are somewhat unique among environmental contaminants in that they are intentionally synthesized and have economic value which is based on their effect on living organisms and upon their time persistence. The presence of such compounds and the possibility of their accidental or intentional contamination of water supply systems and other environmental resources needed for life support motivates an intense need for monitoring and measuring instrumentation capable of responding to small concentrations of such materials.

Presently available water pollution monitoring instrumentation, for example, varies widely in its achieved measurement accuracy and its portability. A high accuracy but low portability water monitoring function can be accomplished by transporting samples to a central and well-equipped laboratory at one end of the monitoring spectrum, and also by the use of portable analytic instruments carried to the location of possibly contaminated water at the other end of this spectrum. The arrangement of the present invention offers a desirable intermediate capability that lies between these two extremes of the monitoring spectrum in the form of a reasonable small and portable and accurate instrument which is also low in cost and reasonable simple to operate and maintain.

The present monitoring system is based on the use of ion selective membranes. Previous considerations of ion selective membranes include an investigation and technical journal article written by J. H. B. George and R. A. Courant, titled "Conductance and Water Transfer in a Leached Cation-Exchange Membrane", which was published in the Journal of Physical Chemistry, Volume 71, page 246, January 1967, and describes the phenomenon of conductance in membrane structures for a variety of materials including alkaline metals and alkaline earths. The properties of ion exchange membranes in the presence of sodium chloride in solution is described in the article "Electrostatic Phenomena in Ion Exchange Membranes" written by S. D'Allessandro and A. Tantillo, appearing at Volume 9, page 225 in the journal "Desalination," a publication from The Netherlands, published in 1971. An early article regarding ion conductivity appeared in the journal "Z. Electrochem," a publication from West Germany, Volume 55, No. 6, page 475, August 1951, and was authored by J. Mancke and K. F. Bonhoeffer. The disclosure of these publications is hereby incorporated by reference into the present document.

As indicated by these publications, the use of ion selective diffusion membranes for certain purposes is known in the art. The use of such membranes for sensing ions of the type considered in the present invention has not been considered in the prior art however.

SUMMARY OF THE INVENTION

In the present invention, a particular form of diffusion membrane is combined with a sensitive and low complexity resistance sensing apparatus and a procedure for operating this resistance measurement apparatus in order to detect small changes in electrical resistance or electrical conductivity resulting from the presence of contaminant ions in a liquid effluent such as drinking water. The ions of greatest interest in the invention are produced by the incidents of chemical warfare or similar agents appearing in liquid, vapor or aerosol form near the surface of the water.

An object of the present invention therefore is to provide an improved electrical resistance measurement arrangement for selective membranes that are received in a liquid effluent.

It is another object of the invention to provide a membrane resistance measurement arrangement which operates on a differential or small difference between two large signals concept.

It is another object of the invention to provide a membrane resistance measurement which uses optimum values of electrical voltage amplitude and frequency for sensing membrane resistance changes.

It is another object of the invention to provide electrolytic cell arrangements which are suitable for use in making absolute membrane resistance measurements.

It is another object of the invention to provide electrolytic cell arrangements which compensate for perturbations contributed by the instrumental configuration.

It is another object of the invention to provide a sensitive and selective impurity ion detection arrangement that is small, rugged, inexpensive, simple to operate, and provides accurate results.

It is another object of the invention to provide a chemical warfare agent detector that is capable of providing qualitative measurement of agent exposure levels.

Additional objects and features of the invention will be understood from the following description and the accompanying drawings.

These and other objects of the invention are achieved by an electrolytic measurement apparatus which includes the combination of a first electrolytic measurement cell of the fixed position electrode type, a second electrolytic measurement cell of the adjustable electrode position and two electrode chambers separated by a diffusion membrane type, a source of alternating current energy coupled to said first and second electrolyte cells in phase opposition; first and second adjustable electrical resistance elements connected in electrical series with said alternating current energy source and said first and second electrolytic cells respectively; first and second adjustable electrical reactance elements connected in electrical series with said alternating current energy source, said first and second adjustable electrical resistance elements and said first and second electrolytic cells respectively; an electrical null indicating arrangement connected to indicate electrical unbalance between a first series electrical path which includes said energy source, said first electrolytic cell, said first electrical resistance element and said first electrical reactance element and a second series electrical path which includes said energy source, said second electrolytic cell, said second electrical resistance element and said second electrical reactance element.

BRIEF DESCRIPTION OF THE DRAWINGS

FIG. 3 in the drawings including the views of FIGS. 3A and 3B shows a fixed electrode selective diffusion membrane arrangement of an electrolytic cell usable with the FIG. 1 apparatus, FIG. 4 in the drawings shows an alternate arrangement of an electrolytic measurement cell in accordance with the invention.

DETAILED DESCRIPTION

Figure 1:
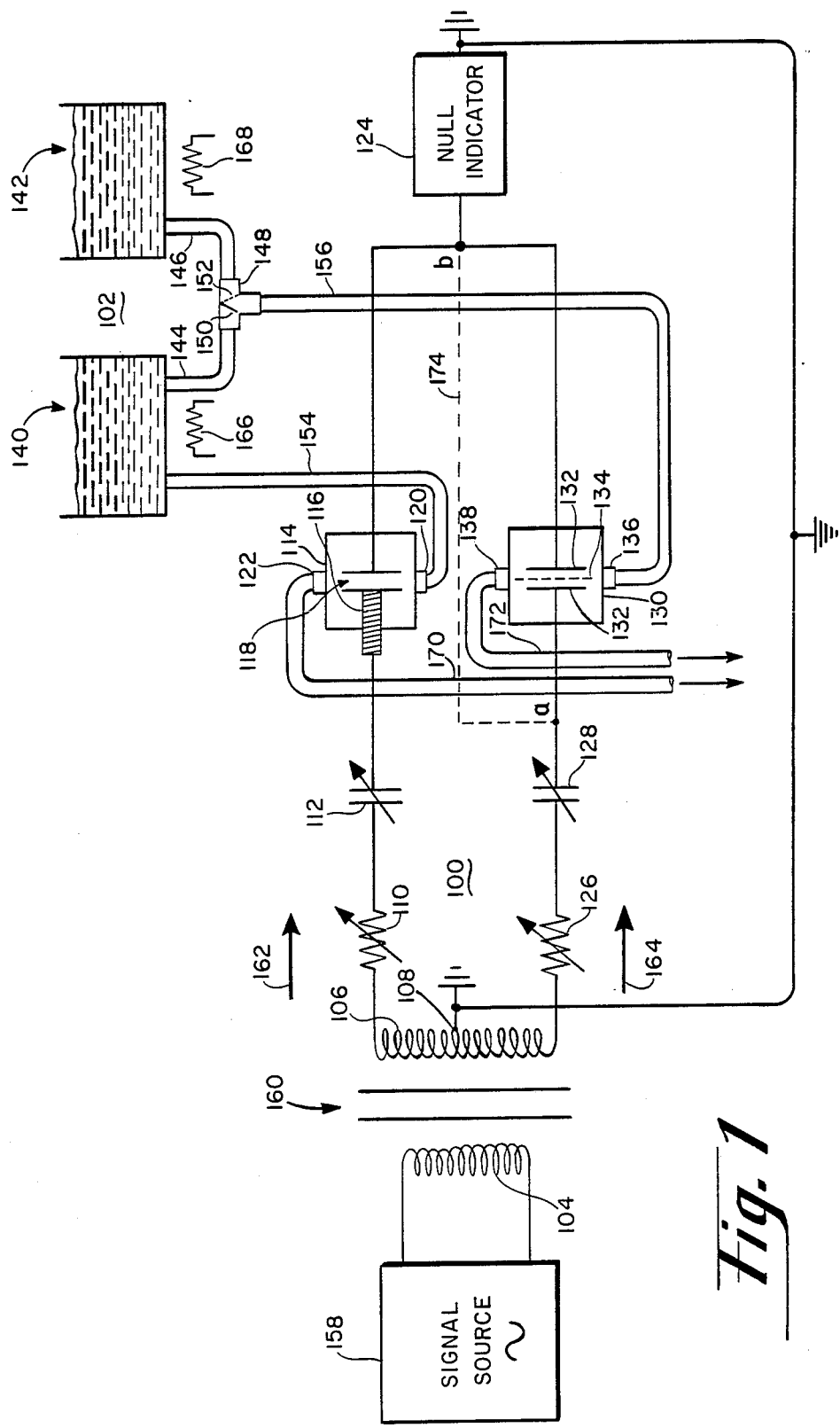
FIG. 1 in the drawings shows a combined electrical and effluent schematic diagram of a measurement apparatus made in accordance with the invention.

FIG. 1 in the drawings shows a combined electrical and effluent schematic diagram of an apparatus made in accordance with the present invention. The FIG. 1 apparatus generally includes an electrical bridge circuit 100, an effluent liquid supply system 102, a signal source 158 for the bridge circuit 100 and a null detector apparatus 124 for detecting the degree of balance in the bridge circuit 100. The bridge circuit 100 includes the secondary winding 106 of a coupling transformer 160, a pair of adjustable electrical resistance elements 110 and 126, a pair of adjustable electrical capacitor element 112 and 128, and a pair of electrolytic resistance measurement cells 114 and 130.

The bridge circuit 100 is electrically energized by a source of alternating signal 158 which is preferably sinusoidal in nature. Signal energy from the source 158 is coupled into the transformer 160 by way of the transformer primary winding 104. The degree of balance in the bridge circuit 100 is measured by a null detector circuit 124 which may have the form of a high input impedance oscilloscope or other low level signal responsive device such as a volt meter, an audio frequency amplifier with an attached electrical to acoustic transducer device such as headphones or loud speaker. The frequency response capability of the null detector device selected should be several times, preferably ten times, the frequency of the signal source 158 in order that harmonic signal components introduced in the bridge circuit elements be detectable.

The electrical circuit path which includes the upper portion of the transformer secondary winding 106, that is the portion between the center tap 108 and the electrical resistance element 110, together with the resistance element 110, the capacitor element 112, and the measurement cell 114 may be collectively referred to as one arm of the bridge circuit 100; this arm is indicated by the arrow 162 in FIG. 1. In a similar manner, the arrow 164 refers to the arm of the bridge circuit which includes the lower half of the secondary winding 106, the resistance element 126, the capacitor element 128 and the electrolytic measurement cell 130.

The electrolytic measurement cell 114 in the upper arm 162 of the bridge circuit 100, is shown to include a pair of electrolyte immersed electrode members 118, a threaded adjustment member 116 for altering the spacing of the electrode members 118 and inlet and outlet connections 120 and 122 for conveying electrolytic effluent into and out of the measurement cell 114. The conduits 154 and 170 convey the liquid electrolyte effluent to and from the connections 120 and 122.

In a similar manner, the electrolytic measurement cell 130 in FIG. 1, the cell of the bridge arm 164, includes a pair of fixed position electrodes 132, effluent inlet and outlet connections 136 and 138 which are coupled to the conduits 156 and 172 and also includes a diffusion membrane member 134 that is disposed between the electrodes 132 in the fluid path between the connections 136 and 138.

The effluent liquid supply system 102 in FIG. 1 is shown to include a reservoir of standard or uncontaminated purging effluent 140 which connects to the movable electrode measurement cell 114 by way of the conduit 154 and connects to the fixed position measurement cell 130 by way of the conduits 144 and 156 and the valve member 148. The effluent liquid supply 102 also includes a reservoir of possibly contaminated or unknown effluent liquid 142 which connects to the membrane containing measurement cell 130 by way of the conduits 146 and 156 and the valve 148. The movable member 150 is included in the valve 148 to select between the effluent reservoirs 140 and 142, the movable member being disposable in the alternate position indicated by the dotted line at 152 when effluent from the reservoir 140 is to be received in the measurement cell 130 and disposed as shown in FIG. 1 when effluent from the reservoir 142 is to be received.

The effluent in the conduits 154, 144 and 156 may, of course, be electrically conductive and thereby provide an electrical path of some significance between the arms 162 and 164 of the bridge 100. The electrical significance of this "leakage" path is, of course, dependent upon its length, that is, on the physical length of the conduits 154, 144 and 156 and other variables. As described below, however, use of the FIG. 1 apparatus preferably includes a preliminary balancing sequence in which the bridge 100 is pre-balanced without the presence of membrane 134 but with other bridge conditions, including the leakage path, in the same condition as when the bridge is in use with the ion sensitive membrane. By way of this preliminary balancing and the possible selection of significant physical lengths for the conduits 154, 144 and 156, the effect of this arm-to-arm conduction path is negated in the results provided by the FIG. 1 apparatus. Alternately, the effect of this leakage path can be minimized by introducing a discontinuity such as an air gap or air bubble or electrical isolation valve into the conduits of the arm-to-arm path prior to performing electrical measurements.

The effluent liquid supply system 102 also includes a temperature control apparatus for each of the reservoirs 140 and 142 as is indicated by the electrical heater elements 166 and 168 in FIG. 1. This temperature control apparatus preferably includes electrical heaters, thermostats and other liquid temperature control elements as are known in the art. Preferably, the temperature control arrangement is made capable of holding the liquid effluent supplied to the cells 114 and 130 at a temperature in the range of 25° C. with a temperature tolerance of 0.1° C. between reservoirs 140 and 142 and maximum temperature excursions of ±5° C.

Figure 2:
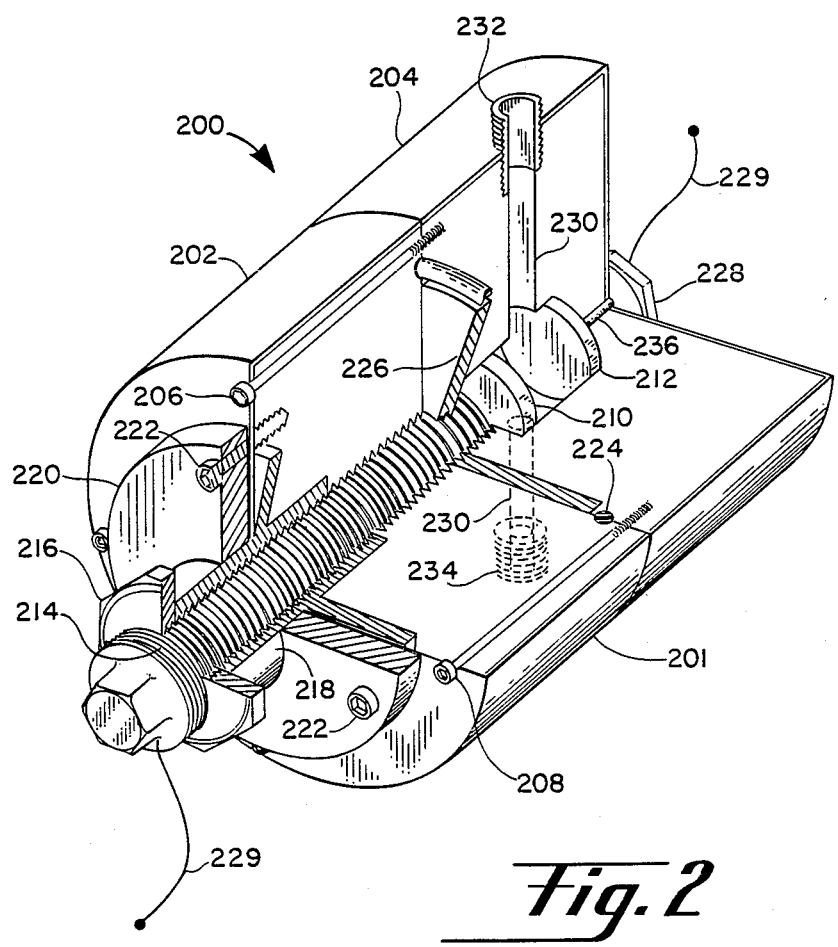
FIG. 2 in the drawings shows a movable electrode electrolytic cell arrangement usable in the FIG. 1 arrangement of the invention.

Additional details concerning a desirable form of an electrolytic measurement cell for the present apparatus are shown in FIG. 2 of the drawings. The FIG. 2 electrolytic measurement cell 200 includes a housing member 201 which is comprised of left and right segments 202 and 204 that are held in the relative assembled position shown in FIG. 2 by the machine screws or the like shown at 206 and 208. Received in the housing segment 204 are a pair of electrode members 210 and 212 that are also disposed along an effluent communicating path 230 and connected with the exterior surface of the housing member 201 by a metallic conductor 236 and a threaded electrode positioning member 214. The active areas of the electrode member 210 and 212 are preferably as identical in nature as is attainable and may be fabricated by sputtering or electroplating a material such as platinum over a base metal such as aluminum or silver. Preferably the sputtering or plating operations are conducted simultaneously and in the same vacuum chamber or plating bath in order to achieve the greatest possible similarity between electrode materials.

The FIG. 2 measurement cell 200 also includes a threaded bushing member 218 and a bushing retaining collar member 220 which is attached to the housing segment 202 by machine screws or the like shown at 222. A lock nut 216 is used to retain the electrode positioning member 214 in an achieved position in the threaded bushing 218.

Additional details of the measurement electrode apparatus shown in FIG. 2 include the resilient O-ring member 224 which serves to seal the interface between housing segments 202 and 204, the threaded electrode sealing member 226 which serves to block the possible flow of liquid effluent from the communicating path 230 along the junction of the threaded electrode positioning member 214. Electrical connections to the measurement cell 200 of FIG. 2 are made by way of the hexagon nut 228 and leads 229 or similar electrical connecting arrangements. Liquid effluent inlet and outlet port structures are indicated at 232 and 234 in FIG. 2 with the illustrated port arrangement representing the use of inert plastic fittings or the like.

The housing segments 202 and 204 in FIG. 2 are preferably fabricated from machinable inert plastic materials such as the polycarbonate material known as Teflon ®, or from other chemically inert and electrically insulating materials as are known in the art. The sealing member 226 is preferably made of Kapton ® or a similar resilient flexible inert material which is capable of preventing leakage of the liquid effluent from the path 230 back along the sides and threads of the positioning member 214. Sealing is important in the FIG. 2 cell in order to preclude loss of the liquid effluent material into the testing environment—a loss which could be undesirable in the case of effluent other than uncontaminated water being tested, and also to limit the tendency for electrode action to occur along the circumference of the positioning member 214.

FIG. 3A of the drawings shows additional details of a membrane containing fixed electrode position measurement cell of the type indicated at 130 in FIG. 1. In the FIG. 3A measurement cell 300, a pair of mating housing segments 302 and 304 are shown to meet in an interface junction 320 that is sealed by a resilient O-ring member 322 with the housing segments being retained in the illustrated position by machine screws or the like shown at 306, 307, and 308. The see-through or X-ray perspective nature of the measurement cell view in FIG. 3A is indicated by the dotted cutting line 301 which, of course, does not appear in a physical embodiment of the cell 300. The electrodes of the FIG. 3A cell, shown at 310 and 312, are each of a fixed position nature and are otherwise similar to the electrodes 210 and 212 in the FIG. 2 cell. In the FIG. 3A cell, the electrodes 310 and 312 are connected with external terminals which are illustrated in the form of the hexagon nuts 336 and 338 by metallic conductor members 314 and 316, respectively. The electrodes 310 and 312 are intended to be circular in nature but are shown in a cutaway condition in FIG. 3A for drawing convenience.

Disposed between the electrodes 310 and 312 in the FIG. 3A measurement cell is a selective ion diffusion membrane which is indicated in exaggerated form at 318 in the FIG. 3A drawing. Two effluent communicating paths 332 and 334 are provided in the FIG. 3A measurement cell. One of these paths traverses the face of each of the electrodes 310 and 312. The path 332 commences with the inlet port 340, and includes the inlet conduit 328, the outlet conduit 324, and the outlet port 346. The path 334 commences with the inlet port 342 and includes the inlet conduit 330, the outlet conduit 326 and the outlet port; the path 334 also traverses the face of the electrode 312 as is indicated by the arrow 335. The paths 332 and 334 are physically and electrically isolated from each other within the cell 300 except, of course, for ionic transmission that occurs across the membrane 318. A cross-sectional view of the FIG. 3A cell is shown in FIG. 3B where the nature of the paths 332 and 334 is more clearly visible.

Even though separate paths for the liquid effluent on opposed sides of the membrane 318 are provided in FIGS. 3A and 3B, it is desirable for the effluent on opposite membrane sides to be the same, to promote membrane absorption of the contaminate or other unknown ions equally on both sides of the membrane and to prevent membrane buckling or distortion. Although not shown in the FIG. 1 illustration of a measurement system, this same effluent on both sides of the membrane 318 may be achieved with the use of a tee fitting in the conduit 156 at some point prior to the cell 300. Electrical conduction through this tee fitting, that is, the electrical leakage between electrodes 310 and 312 via the tee fitting effluent is removed from consideration in the measurement accomplished with the FIG. 1 apparatus by the preliminary balancing or air discontinuity concepts that were described above.

It is desirable for the membrane 318 to have a physical diameter that is larger than that of the electrodes 310 and 312 in order that edge effect be minimized or predictable. Edge effect considerations in a cell of the FIG. 3A type are described in the technical article "Permeation Through a Membrane with Mixed Boundary Conditions", authored by R. M. Barrer, J. A. Barrie, and M. J. Rogers, appearing in the British publication "Transactions of the Faraday Society," Volume 58, No. 480, page 2473, December 1962. The disclosure of the Barrer, Barrie and Rogers article is hereby incorporated by reference herein.

The physical dimensions of the FIG. 3A electrical chemical cell and those of the ion exchange membrane can be expected to have a significant influence on the sensitivity and accuracy of the differential difference method described herein. The sensitivity of the described measurement arrangement will increase with decreasing values of inter-electrode separation in the FIG. 3A cell and with increasing diameter of the electrode chambers. Inter-electrode separations in the FIG. 3A cell are preferably maintained above a value of three millimeters in, for example, a cell with an electrode diameter of 30 millimeters or greater. This resulting one to ten electrode separation to diameter ratio minimizes the possibility of an ion exchange membrane directly contacting either electrode as a result of membrane swelling or buckling. Preferably however, the internal chamber diameter and the electrode diameters in the FIG. 3A cell are on the order of ten millimeters with the membrane diameter being at least 15 millimeters in response to edge effect size limitations described in the above referenced publication.

The housing segments 302 and 304 of the FIG. 3A cell are also preferably made from a machinable inert and electrically insulating material such as the FIG. 2 preferred material of Teflon ®. Membranes suitable for use at 318 in FIG. 3A are commonly available in the commercial marketplace; suitable membranes for use in the present apparatus are, for example, manufactured by Ionics, Inc. of Cambridge, MA and are known generally as ion-selective, highly-crosslinked polymeric membranes.

Returning now to the schematic diagram of FIG. 1 in the drawings, once the electrolytic measurement cells of FIGS. 2 and 3A have been connected into the bridge circuit 100, the above described initial balance condition is to be achieved. This initial balance is accomplished with the membrane 134 in FIG. 1, or 318 in FIG. 3A, removed from the membrane cell. The initial balance condition is accomplished after both electrolyte cells 114 and 130 in FIG. 1 have been purged with a standard uncontaminated and temperature controlled effluent as supplied by the resevoir 140. The initial balance condition is accomplished by switching the movable valve member 150 to the possibly contaminated or unknown effluent liquid 142 with the resistance and reactive elements 110, 126 and 112, 128 in the zero condition using the threaded adjustment member 116 in the cell 114. The achievement of balanced condition is sensed by a voltage minimum condition at the null indicator 124. Once the desired voltage minimum condition is obtained, the electrode 210 and positioning member 214 in the FIG. 2 embodiment of the cell 114 are locked into the attained position using the lock nut 216.

Following positioning of the movable electrode 210 in the initial balance operation any residual inbalance, which may result, for example, from unavoidable differences in the state of the electrode surfaces, is removed by adjusting the variable capacitors 112 and 128 as needed in order to optimize the null observed by the detector 124. As a result, the equilibrium impedance condition in the arms of the electrical bridge 100 can be expressed as:

$$z_1 + R_1 + z_2 = z_3 + R_2 + z_4 \qquad (1)$$

where $z_1$, $z_2$, $z_3$ and $z_4$ are the complex impedances of the respective electrode/solution interfaces and include the Gouy-Chapman layer effect and other geometric effects, and $R_1$ and $R_2$ are the resistances of the solution in cells 114 and 130 respectively.

After the impedance in each arm of the bridge 100 is initially balanced, the ion-exchange membrane of interest 134 with characteristic resistance $R_x$, is inserted in the cell 130. Membrane insertion and removal can be accomplished easily by disposing the membrane in a carrier, similar to the arrangement used for 35 millimeter color slide viewing, for example, and pivotally mounting the carrier to rotate either the membrane or a non membraned open aperture between the electrodes of the measurement cell.

Insertion of the ion selective membrane can be expected to add a principally resistive component to the arm 164 of the bridge 100. Such a resistive or Ohm's Law behavior addition is known in the membrane art and is to be expected so long as the potential across the measurement cells does not exceed five volts peak to peak. Resistive behavior also occurs so long as the signal source 158 in FIG. 1 provides bridge excitation with pure sinusoid signals-signals that fall within the frequency range of two to 15 kilohertz. An energizing potential between one and five volts peak to peak with a frequency between two and ten kilohertz is therefore desirable for the bridge 100. Re-balancing of the bridge 100 following insertion of the selective membrane is accomplished using the resistances 110 and 126. As a result, the new condition of equilibrium associated with the electrical network can be expressed as:

$$z_1 + R_1 + z_2 + R_{M1} = z_3 + R_2 + z_4 + R_{110} \qquad (2)$$

Since all of the parameters, except $R_{M1}$, remain constant after a new null or voltage magnitude minimum is achieved, it follows that:

$$R_x = R_{M1}. \qquad (3)$$

Finally, to complete the differential difference measurement method, segment $a \neq b$, the path 174, of the FIG. 1 circuit, is completed with a conductor. As a result, a determination of the concentration of the solution in equilibrium with the ion-exchange membrane can now be simultaneously accomplished with the measurement of absolute resistance of the membrane itself —via the change or differential in equation (3) above. The shorting connection between points a and b in FIG. 1, the path 174, should be accomplished and removed several times with a new reading and arithmetic averaging of the new reading at each short removal to ensure that the bridge circuit has been accurately nulled. The actual number of contaminant ions present in a unit volume of effluent, the number of ions per cubic centimeter, for example, may be correlated with the resistance change necessary to achieve final bridge balance using a predetermined graph, or chart or a computerized look-up table in order to simplify the relation of impedance to contaminant concentration. Since ion effect on the membrane 134 can be expected to change with continuing flow of the effluent from the reservoir 142, bridge balancing activities are preferably accomplished in the presence of stationary or no flow conditions in the cells 118 and 130. Purge solution should be utilized to thoroughly flush the cells between measurements involving a solution which may be contaminated. Non zero values of the resistance $R_{126}$ in FIG. 1 allow proportional division of current between bridge arms for high ionic solution concentrations, concentrations tending to produce very low membrane resistance values. During the more frequent low normality solution measurements zero resistances at $R_{126}$ are satisfactory.

The described differential difference measurement method reduces the systematic error in the measurement of an ion-exchange membrane's electrical resistance when concentrations as low as the iso-conductivity point are investigated (typically 0.001 to 0.1 normal (N). The relative error ($\delta$), which is manifested during the initial electrical balancing of the electrochemical cell, can be estimated using the electrode-solution impedance identified above and component identification in FIG. 1 and the magnitude of the voltage level (V) measured between one end terminal and the center tap of the secondary winding 106 ($V_{106}$) and the magnitude of the voltage minimum ($V_{min}$) detected with the null indicator 124 as follows.

After the initial equilibration of the electrical bridge, equation (1) and the assumption that $(z_1+z_2=z_3+z_4)$, implies that:

$$V_{min} = |(V_{106}/R_{110})| \times |(R_{110}-R_{126})| \quad (4)$$

from which it follows that:

$$\delta = (R_{110}-R_{126})/R_{110} = V_{min}/V_{106}. \quad (5)$$

Following the placement if the ion-exchange membrane in chamber 130, and the accomplishment of the adjustments necessary to establish a new null or voltage minimum, it follows that:

$$V_{min} = |(V_{106}/(R_{110}+R_{130})| \times \{|(R_{110}-R_{126})| \pm | (R_{130}-R_{114})|\}. \quad (6)$$

Selecting the plus sign in equation (6) yields the upper bound of the differential difference measurement method's error, and the transformation implied by equation (5) yields:

$$\delta X = (R_{130}-R_{114})/R_{130} = \delta((2R_{110}/R_{130})+1). \quad (7)$$

Thus, the error introduced by the differential difference measurement is random, and its magnitude will be a small value by virtue of the fact that a deliberate succession of impedance balancing operations has minimized the contributions and influence of the physical hardware.

ADVANTAGES AND NEW FEATURES

The advantages and features of the invention include the following:

1. The measurement apparatus of the invention resolves a performance limitation associated with many present-day electrochemical cells by utilizing a differential-difference measurement method to identify the true electrical resistance of an ion-exchange membrane—that is, compensation is provided for the transitional resistance perturbations of the cell's electrode/membrane and membrane/ membrane phase boundaries. The resistance of the cell's chamber filled with the uncontaminated electrolyte, is excluded from the measured electrical resistance of the cell with both the electrolyte and the ion-exchange membrane.

2. The electrochemical cell includes two independent chambers and four electrodes. Three electrodes are fixed and the fourth is movable. This feature permits the accurate differential-difference measurement method to be implemented.

3. Measurement errors are reduced to those that are random in nature and have a small magnitude; repeated measurements of a given state followed by arithmetical averaging will further reduce the significance of such measurement errors.

4. The disclosed cell design minimizes the possibility of deformation or other undesirable direct contact between the ion-exchange membrane and the adjacent cell structure.

5. The disclosed cell dynamic solution flow-through scheme facilitates the measurement of the concentration dependence of the electrical conductivity in an ion-exchange membrane without cell disassembly each time a new solution is characterized.

6. The concept, design and method of collecting data are generalized; universal application for a plurality of ion-exchange membranes and a host of ionic solutions is possible.

7. The sensitivity of the electrochemical cell permits measurement of electrical resistance in an ion-exchange membrane when ionic concentrations as low as the iso-conductivity point are investigated—typically for 0.001 to 0.1 normal (N) solutions.

Numerous modifications of the disclosed embodiment are possible within the bounds of the overall invention. Among these modifications are a measurement cell having both electrodes fixed but without a selective membrane, that is, the placement of both the movable electrode and the selective membrane in a single one of the cells 114 and 130 in FIG. 1. An arrangement of this type may be somewhat more difficult to balance, however.

Figure 4:
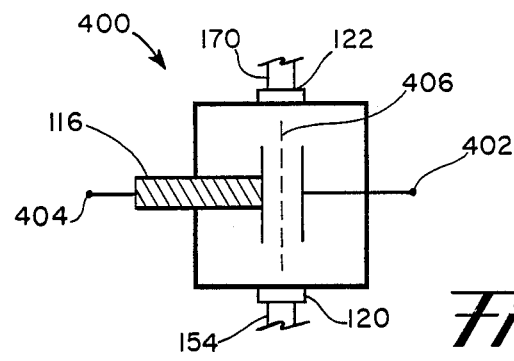

Another possible modification of the method and apparatus disclosed herein involves use of the bridge circuit 100 as a measurement device for determining ohmic resistance of an electrolytic cell or a membrane. By shorting one of the cells 114 and 130 in FIG. 1, as shown at 174, the remaining bridge circuit can be used to measure ohmic resistance values in the manner of a Wheatstone or other known bridge circuits. Another arrangement of an electrolytic measurement cell in accordance with the invention is shown at 400 in FIG. 4 of the drawings. The cell 400 is similar to the cell 114 in FIG. 1 except for incorporation of both position adjustable electrodes and the ion selective membrane 406 in the FIG. 4 cell. The similar parts in the FIG. 4 cell 400 and the FIG. 1 cell 114 are, in fact, identified with the same numbers taken from FIG. 1 in both cells. The FIG. 4 cell 400 may be used in measuring ohmic resistance values using the terminals 402 and 404. Such values are dependent on the employed selective membrane, electrode, and electrolyte characteristics within the cell 400.

Since the disclosed ion selective membranes tend to respond preferentially to different ions, that is, since these membranes are element selective in nature, the use of plural bridge circuits or plural electrolytic cells for one bridge circuit may be desirable in instances where the effects of several different contaminant ions are to be detected or measured.

While the apparatus and method herein described constitute a preferred embodiment of the invention, it is to be understood that the invention is not limited to this precise form of apparatus or method, and that changes may be made therein without departing from the scope of the invention, which is defined in the appended claims.

I claim:

1. Electrolytic measuring apparatus comprising the combination of:

a first electrolytic measurement cell having first and second electrodes that are disposed in adjustable electrode separation;

a second electrolytic measurement cell having fixed position electrodes and two electrode chambers that are separated by a diffusion membrane;

a source of alternating current electrical energy coupled to said first and second electrolytic cells in phase opposite polarities;

first and second adjustable electrical resistance elements connected in electrical series with said alternating current energy source and said first and second electrolytic cells, respectively;

first and second adjustable electrical reactance elements connected in electrical series with said alternating current energy source, said first and second adjustable electrical resistance elements, and said first and second electrolytic cells, respectively;

electrical null indicating means connected to indicate electrical unbalance between a first series electrical path which includes said energy source, said first electrolytic cell, said first electrical resistance element and said first electrical reactance element and a second series electrical path which includes said energy source, said second electrolytic cell, said second electrical resistance element and said second electrical reactance element.

2. The apparatus of claim 1 wherein one of said first and second electrolytic measurement cells is of the flow through type.

3. The apparatus of claim 2 wherein said source of alternating current energy includes a center tapped transformer winding and wherein first and second halves of said center tapped winding are connected in said phase opposite polarity with said first and second series paths, respectively.

4. The apparatus of claim 3 wherein said membrane is of the ionic selectively permeable type.

5. The apparatus of claim 4 wherein said selectively permeable ionic membrane is selective of ions which include one of the chemical elements of phosphorous, chlorine, sulfur, and fluorine.

6. The apparatus of claim 1 wherein said source of alternating current energy has a sinusoidal waveform shape.

7. The apparatus of claim 1 wherein said adjustable electrical reactance elements comprise electrical capacitors.

8. The apparatus of claim 1 wherein said electrical null indicating means is connected between the junctions of said first and second series electrical paths and said transformer winding center tap.

9. The apparatus of claim 8 wherein said electrical null indicating means has a frequency response spectrum that is at least ten times the fundamental frequency of said source of alternating current energy.

10. The apparatus of claim 9 wherein said null indicating means comprises an oscilliscope.

11. The apparatus of claim 1 wherein said first and second electrolytic measurement cells include platinum electrodes.

12. The apparatus of claim 1 wherein said source of alternating current energy has a peak to peak amplitude between one and five volts and a frequency between two and ten kilohertz.

13. An electrolytic cell and electrical bridge circuit method for measuring changes in low concentration unknown electrolyte conductivity, said method comprising the steps of:

connecting a first electrolytic cell having adjustable electrode separation and a second electrolytic cell having fixed electrode separation and a removable ion selective membrane into first and second arms of an alternating current electrical bridge circuit;

immersing said electrodes in said cells in identical unknown electrolyte solutions;

adjusting the electrode separation in said first electrolytic cell to the condition of best attainable electrical balance in said alternating current bridge circuit with said membrane in the removed condition;

adding electrical capacitance to the arms of said electrical bridge circuit to optimize the bridge balance;

introducing said removable ion selective membrane to said unknown solution filled fixed electrode cell;

altering the electrical resistance values in said bridge arms until an optimum rebalanced condition results;

determining from the resistance altering in said altering step the electrical resistance attributable to said membrane and unknown electrolyte ionic conduction therein.

14. The method of claim 13 wherein said unknown solution comprises a compound that is ionizable in said electrolyte.

15. The method of claim 14 wherein said ionizable compound includes one of the chemical elements phosphorous, chlorine, sulfur or fluorine.

16. The method of claim 14 further including the step of correlating said membrane cell electrical resistance change with the concentration of said ionizable compound in said electrolyte solution.

17. The method of claim 15 wherein said ionizable compound is disposed in one of the physical states of a gas, a vapor and an aerosol prior to reception and ionization in said electrolyte solution.

18. The method of claim 15 further including the steps of introducing said unknown electrolyte solution to a plurality of said electrolytic cell and bridge circuit combinations, each electrolyte cell and bridge circuit combination including a different selective ion membrane.

19. The method of claim 18 wherein said different selective ion membranes are each selective of one chemical warfare agent ion taken from the group of phosphorous ions, chlorine ions, sulfur ions, and flourine ions.

20. The method of claim 13 further including the steps of electrically shunting one of said electrolytic cells with a low impedance conductor and measuring the electrical resistance of said remaining electrolytic cell.

21. An electrolytic measurement apparatus comprising the combination of:

a measurement cell body member comprised of rigid electrically insulating material;

a fluid flow path extending through a portion of said body member and terminating in flow path ports received on said body member;

a first fixed position electrode member received along said flowing path in communication with fluids flowing therethrough, said electrode member including electrical conductor means communicating between said electrode member and a first electrical terminal member received on said body member;

a second adjustable position electrode member received along said flow path in communication with fluids flowing therethrough, said second electrode member including position adjusting means in communication with a second electrical terminal of said cell for precisely altering the relative position of said second electrode member with respect to said first electrode member;

sealing means communicating between said adjustable position electrode member and said body member for restraining leakage flow of electrolyte between said flow path and the exterior of said cell along said adjustable position electrode member;

a selective ion diffusion membrane member disposed intermediate said first and second electrode members in said fluid flow path;

means for measuring incremental values of electrical resistance between said first and second terminals.

22. The apparatus of claim 21 wherein said electrode members and said membrane member are each of a circular shape with said membrane member having a diameter greater than said electrode members.

23. The apparatus of claim 21 wherein said electrode members are comprised of metallic platinum.

24. A chemical warfare agent detector for water supply and other fluids comprising the combination of:

an alternating current electrical bridge circuit having one each of an unknown and reference electrolytic measurement cell element and an electrical impedance element disposed in each of two circuit arms thereof;

an ion selective diffusion membrane member disposed in one of said electrolytic measurement cell elements in the inter electrode electrolyte path thereof, said membrane member being selectively responsive to ions of a predetermined group of chemical warfare agent constituent elements;

means for nulling said electrical bridge circuit in the presence of uncontaminated fluid samples in each of said electrolytic measurement cells;

means for introducing a chemical warfare agent contaminated fluid sample into one of said electrolytic measurement cells;

means to re-balance said bridge circuit in the presence of said warfare agent.

* * * * *

UNITED STATES PATENT AND TRADEMARK OFFICE
CERTIFICATE OF CORRECTION

PATENT NO. : 4,871,427
DATED : October 3, 1989
INVENTOR(S) : Edward S. Kolesar, Jr.

It is certified that error appears in the above-identified patent and that said Letters Patent is hereby corrected as shown below:

Col 6, line 29, after "outlet port" should be "346".

Col 6, line 40, after "same," should be "--".

Col 8, line 36, "a=b" should be "a-b".

Col 8, line 40, "the" should be deleted.

Col 9, line 38, "$\delta X$" should be "$\delta_\chi$".

Signed and Sealed this

Third Day of September, 1991

Attest:

HARRY F. MANBECK, JR.

*Attesting Officer*   *Commissioner of Patents and Trademarks*